United States Patent [19]
Fujita

[11] Patent Number: 5,514,346
[45] Date of Patent: May 7, 1996

[54] DRYER FOR DEODORIZATION AND STERILIZATION

[76] Inventor: Sanai Fujita, 107 Green Park Kotesashi 12-1, 4-chome Kotesashi-cho, Tokorozawa-shi, Saitama-ken, Japan

[21] Appl. No.: 342,807

[22] Filed: Nov. 21, 1994

[30]     Foreign Application Priority Data

| Apr. 1, 1994 | [JP] | Japan | ................................. 6-085289 |
| Apr. 21, 1994 | [JP] | Japan | ................................. 6-105005 |
| Aug. 1, 1994 | [JP] | Japan | ................................. 6-197141 |

[51] Int. Cl.⁶ ................................................. A61L 9/02
[52] U.S. Cl. ................ 422/124; 422/122; 422/306; 261/99; 261/107; 239/54; 392/381; 34/90
[58] Field of Search ............................ 422/4, 5, 37, 120, 422/122, 123, 124, 292, 306; 261/99, 107, 142; 239/34, 54, 57; 392/379, 380, 381, 382, 383, 384, 385, 390; 34/90, 97

[56]     References Cited

U.S. PATENT DOCUMENTS

| 2,517,996 | 8/1950 | Franklin et al. | ................. 392/380 |
| 3,290,112 | 12/1966 | Gillenwater et al. | ................. 392/390 |
| 3,793,744 | 2/1974 | Saita | ................................. 422/5 |
| 3,911,080 | 10/1975 | Mehl et al. | ................. 423/210 |
| 4,343,765 | 8/1982 | Elston et al. | ................. 422/37 |
| 4,383,377 | 5/1983 | Crafton | ................. 422/124 |
| 4,468,372 | 8/1984 | Seifert et al. | ................. 422/4 |
| 4,708,946 | 11/1987 | Ohata et al. | ................. 502/304 |
| 4,732,591 | 3/1988 | Tujisawa et al. | ................. 422/124 |

*Primary Examiner*—Robert J. Warden
*Assistant Examiner*—Theresa T. Snider
*Attorney, Agent, or Firm*—Andrus, Sceales, Starke & Sawall

[57]     ABSTRACT

A deodorizing and sterilizing dryer can readily provide deodorization, sterilization, and mold prevention for various goods, such as shoes, by supplying a deodorizing and sterilizing air stream. The deodorizing and sterilizing dryer includes, at one end, an outlet and, internally, a heater and a fan. Air that is heated by the heater is forced along an air stream path, which lies between the heater and the outlet, and contacts a columnar ceramic body that is impregnated with an acid solution and a columnar ceramic body that is impregnated with an alkaline chlorine dioxide solution. Both ceramic bodies have a plurality of lengthwise through holes, so as to supply deodorizing and sterilizing air that contains chlorine dioxide gas.

29 Claims, 18 Drawing Sheets

DRYER FOR DEODORIZATION AND STERILIZATION

BACKGROUND OF THE INVENTION

1. Field of the Invention

The present invention relates to a deodorizing and sterilizing dryer that discharges deodorizing and sterilizing air that contains chlorine dioxide gas.

2. Description of the Related Art

Conventionally, there are no easy methods that ensure the performance of deodorization, sterilization, and mold prevention for a variety of products and locations: shoes; sportswear and equipment, such as protective wear for kendo and boxing gloves; wigs; stuffed toys; shoe boxes; lockers; indoor sanitary toilets; and refrigerators.

For example, various types of deodorants, deodorizing agents, adsorbents, etc., have been conventionally used in shoe insoles to eliminate bad odors. These, however, have not been effective enough, and they especially do not ensure the easy performance of deodorization, sterilization and mold prevention.

Further, hand dryers (air towels), which are widely used in building lavatories or the like, conventionally can only dry wet hands and cannot sterilize them.

SUMMARY OF THE INVENTION

To overcome the above described shortcomings, it is an object of the present invention to provide a dryer that ensures deodorization, sterilization, and mold prevention for a variety of goods, such as sportswear and equipment, and wigs.

It is another object of the present invention to provide a dryer (air towel) that can simultaneously perform deodorization and sterilization while drying wet hands.

According to the present invention, a deodorizing and sterilizing dryer includes an outlet and, internally, a heater and a fan whereby air that is heated by the heater is forced along an air stream path, which lies between the heater and the outlet, and contacts a ceramic body that is impregnated with an acid solution and a ceramic body that is impregnated with an alkaline chlorine dioxide solution, both ceramic bodies being provided along the air stream path, so as to supply warm air that contains chlorine dioxide gas.

A volatile organic acid is preferable as the acid for the acid solution; and, taking virulence, odors, etc., into account, the use of citric acid is especially preferable. An acid solution wherein the pH is adjusted by an alkali is desirable; for example, a citric acid solution of pH 2 to pH 5, or, more preferably, either pH 3 or pH 4.

In the present invention, a ceramic body is immersed in an acid solution to obtain a ceramic body that is impregnated with the acid solution.

Chlorine dioxide is normally produced by an acid that acts on sodium chloric acid or calcium chloric acid. Since the chlorine dioxide that is thus obtained is very explosive and dangerous, it must be handled very carefully.

Therefore, chlorine dioxide gas that has been stabilized in alkaline water has been developed. The compound is thereafter kept in the stabilized state (the gas is hereafter referred to as "stabilized chlorine dioxide").

According to this invention, a ceramic body is immersed in the stabilized chlorine dioxide solution to obtain a ceramic body that is impregnated with the stabilized chlorine dioxide solution.

The pH of the alkaline stabilized chlorine dioxide solution of the present invention is preferably pH 8 to pH 10. If the pH is lower than 8 or higher than 10, the liberation of chlorine dioxide gas tends to be difficult and the amount of chlorine dioxide gas that is contained in the air stream tends to be decreased.

The impregnating content of an alkaline chlorine dioxide solution is 500 ppm to 3000 ppm when the content is calculated for chlorine dioxide, and is preferably 1000 ppm to 2500 ppm. The chlorine dioxide that is used by the dryer of this invention can be replaced with ozone.

The ceramic bodies that are respectively impregnated with an acid solution and a stabilized chlorine dioxide solution are positioned between the outlet of the dryer and the heater, with the acid-solution impregnated one located on the heater side and the stabilized-chlorine-dioxide-solution impregnated one located on the outlet side.

When a stream of heated air (heated to, for example, 30° C. to 70° C.) from a heater is driven by a fan so that it passes through the absorbent ceramic bodies, the liberation of chlorine dioxide gas is accelerated and the gas content of the warm air increases.

By directing this stream of warm air at a target, such as at the inside of a shoe, the insole, or at gloves, deodorization, sterilization, and mold prevention can be easily performed.

The ceramic bodies used in the present invention absorb an alkaline chlorine dioxide solution well, and when heated air that is driven by a fan contacts and passes through the ceramic bodies, chlorine dioxide gas is generated and is mixed with the warm air.

An alkaline ceramic is normally employed for the present invention. A preferable ceramic contains at least one element that is selected from a group consisting of, for example, powdered animal bone, powdered shells, powdered limestone, and powdered coral.

Another preferable ceramic contains at least one ceramic material that is selected from a group consisting of silica, alumina, and zeolite.

Taking the absorption capability of an alkaline solution into account, a ceramic that contains powdered animal bones is desirable; moreover, when taking absorption speed into account, a ceramic wherein the proportion of powdered animal bones is high, for example, 50 to 80 weight %, is more desirable.

The powdered animal bones can be replaced with another alkaline adsorbent that has a high alkaline solution absorption capability.

An additional agent, such as a binder or a filling agent, is added to these ceramics, as necessary, to form a ceramic body for the present invention.

The powdered animal bones described above are mainly those that are acquired by processing crude bones, especially the bones of cows, horses, sheep, that are commonly disposed of on farms, etc.

The crude bones are cut into an appropriate size for a calcination process, boiled, and calcined at around 900° C. to 1100° C. Since oxidized putrefaction occurs on bones if organic substances that are not components of bone, such as gelatin, fat, protein, and glue, remain, such substances must be completely eliminated.

During the boiling process, most organic substances that are attached not only to the external walls of bones but are also inside pores along the surface of bones can be removed.

When the calcination process is then performed, the remaining organic substance can be removed completely, and simultaneously the humidity (water content) of the bone can be reduced to several percent or less, preferably to almost 0%.

Dependent on the calcining conditions, the bone is dried and maintains its original organization that includes multiple fine pores. After the bone is cooled, it is crushed and then pulverized and formed into a bone powder having a size of about 20 to 200 mesh, more preferably 50 to 100 mesh, by a powdering machine.

The powdered bone has a yield of about 40 weight % of the original crude bone. The composition of the particles includes calcium (about 33 weight %) as a main component, phosphorus (about 16.7 weight %), barium (about 1.03 weight %), sodium (about 0.76 weight %), sulfur (about 0.64 weight %), and some magnesium, potassium, chlorine, amine, iron, and others. Multiple micropores communicate with each other both on the internal and external sides of the particles, which are alkaline.

Bentonite, Japanese acid clay, activated clay, kaolin clay, sericite, pyrophyllite, refractory clay, montmorillonite, or the like may be employed as a binder.

In this invention, the ceramic body may be formed arbitrarily, particulate, spherical, or columnar, as long as the body is impregnated with an acid solution or an alkaline chlorine dioxide solution.

Taking the impregnation by the acid solution or the alkaline chlorine dioxide solution, the discharge of chlorine dioxide gas, and the convenience of the device design into account, a columnar ceramic body is preferable.

Various designs can be used for the ceramic body: a cylindrical ceramic body into which is inserted a hollow pipe having multiple small holes along its longitudinal surface; and a cylindrical ceramic body having a hollow pipe inserted at each end and having a through hole that forms a connection for the hollow portions of the pipes in the ceramic body.

The ceramic body is detachable from the dryer itself; and it can, for example, be provided as a removable cartridge. Then, after a ceramic body has been used for a certain period of time, it can easily be removed and replaced with a new absorbent ceramic body.

To impregnate the above described ceramic body with an acid solution or an alkaline chlorine dioxide solution, a supply device for an acid solution or an alkaline chlorine dioxide solution may also be provided.

In such a case, a supply groove for supplying an acid solution or an alkaline dioxide solution can be formed in the ceramic body as needed. The supply device itself may be detachable from the dryer.

Since the citric acid solution supply device and the alkaline chlorine dioxide solution supply device are detachable from the dryer, an acid solution or an alkaline chlorine dioxide solution can be supplemented rapidly and easily.

In a dryer for deodorization and sterilization according to the present invention, a plurality of small holes are formed on its outlet side to communicate with the outlet and discharge warm air, and a plurality of hollow members for insertion into shoes can be attached. With this arrangement, a plurality of shoes can be deodorized and sterilized at one time.

A deodorizing and sterilizing dryer according to the present invention can be installed in a futon (a thick, quilted bed cover or sleeping pad) drying device, an air cleaner, or an air conditioner. This dryer can eliminate bad odors and germs within a futon drying device, an air cleaner, or an air conditioner.

The dryer of the present invention readily and efficiently supplies a deodorizing and sterilizing air stream.

This air stream is effective for the deodorization and the sterilization of a variety of products and locations. It is capable of deodorizing, sterilizing, and preventing the formation of mold on shoes; sportswear and equipment, such as protective wear for kendo, boxing gloves, and ski shoes; toys, such as stuffed toys; shoe boxes; dressing lockers; indoor sanitary toilets; refrigerators; or the like.

When the air stream is used as an air towel, not only are wet hands dried by the warm air of the air towel, but they can also be adequately sterilized, and deodorized as needed.

DETAILED DESCRIPTION OF THE PREFERRED EMBODIMENT

The preferred embodiment will now be described while referring to the accompanying drawings.

In FIGS. 1 through 10, reference number 1 denotes a dryer body; 2, an outlet; 3, a heater; 4, a fan; 5 and 6, detachable ceramic bodies; 7, through holes provided in each of the ceramic bodies 5 and 6; 8 and 9, grooves for supplying an alkaline chlorine dioxide solution and a citric acid solution, respectively; 10 and 11, supply devices for a chlorine dioxide solution and a citric acid solution, respectively; 12, a switch; and 13, a cord.

Figure 1:
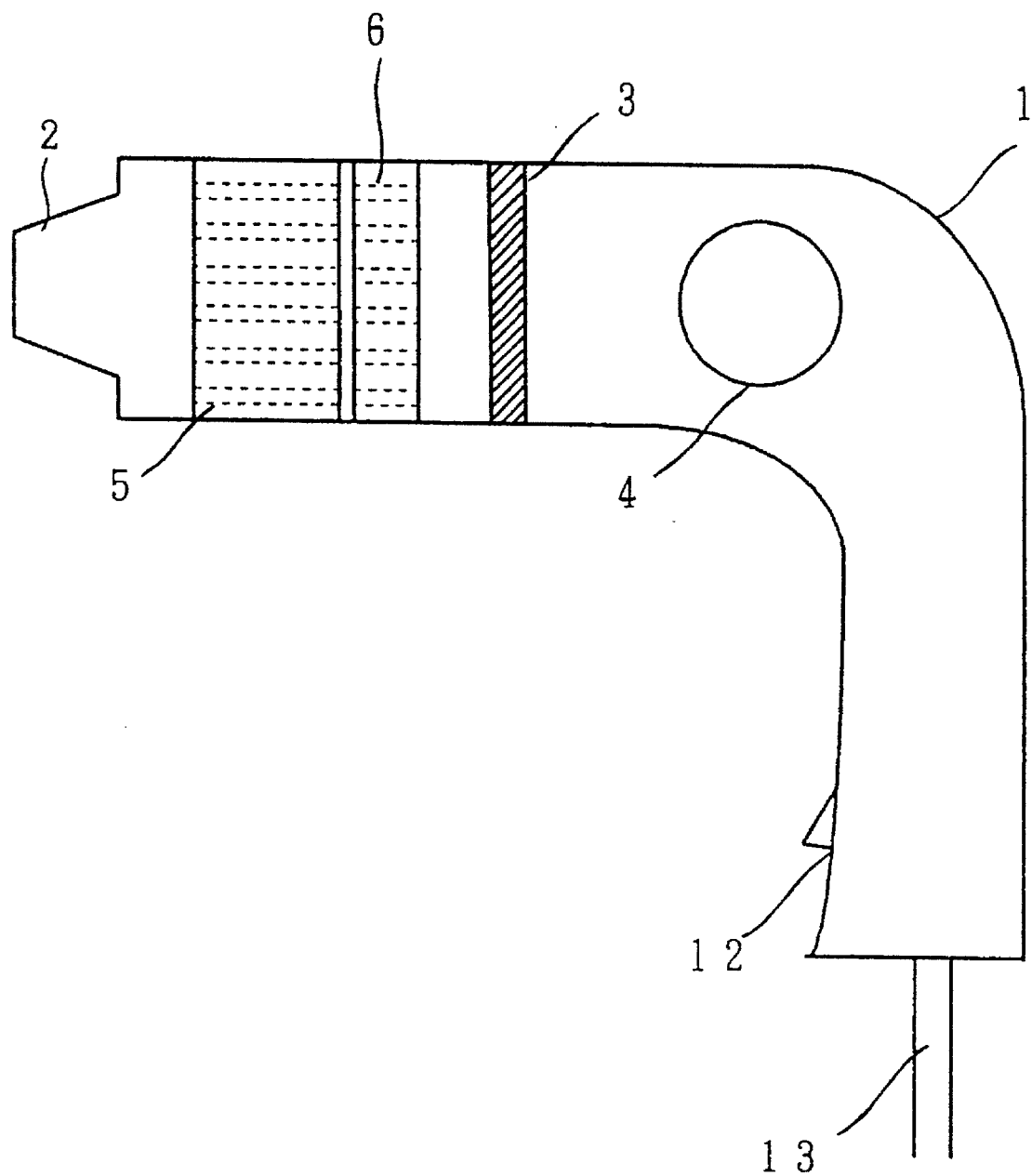
FIG. 1 is a schematic side cross sectional view of an example dryer according to the present invention.
Figure 2:
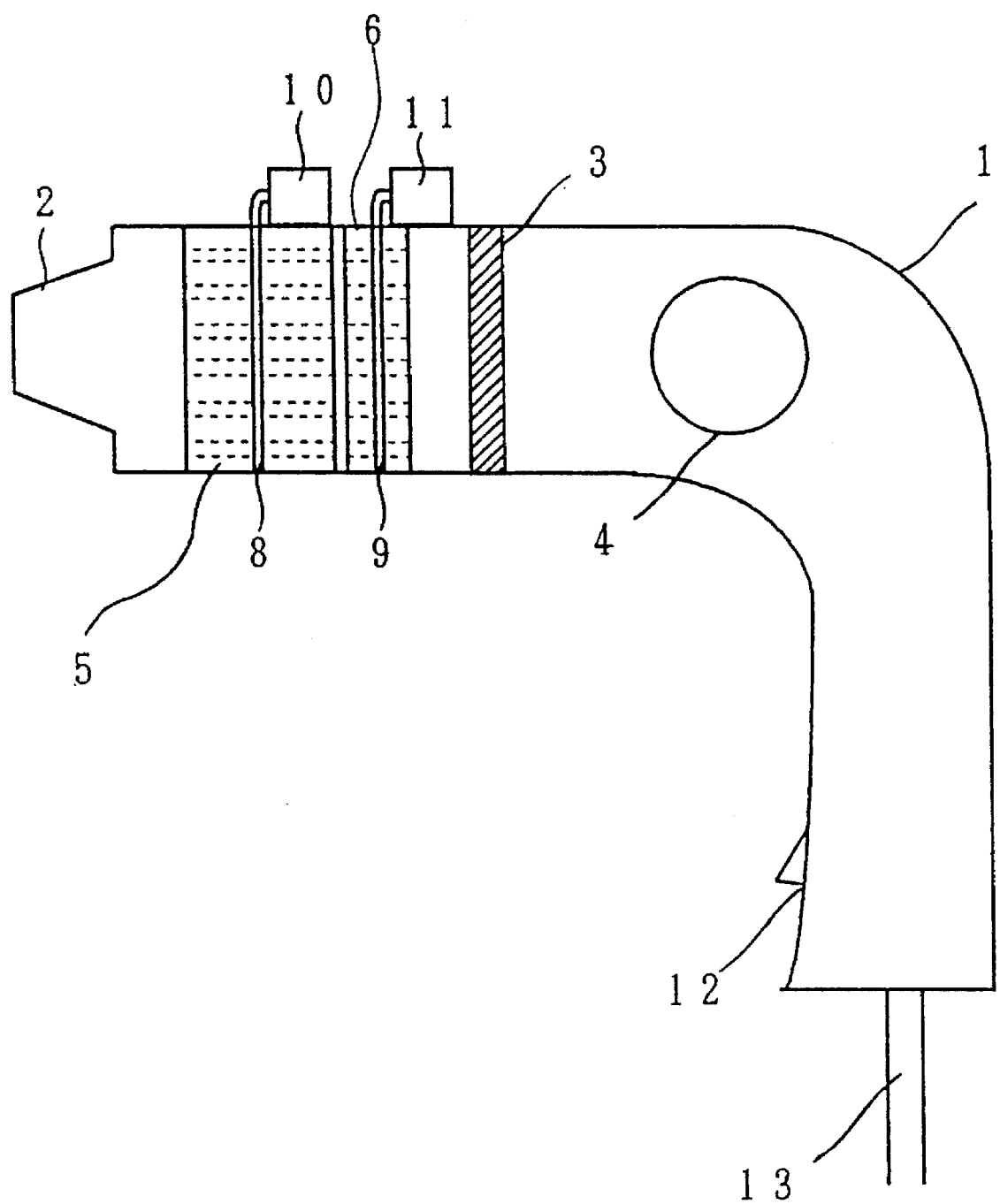
FIG. 2 is a schematic side cross sectional view of another example dryer according to the present invention.

In the examples shown in FIGS. 1 and 2, a portable compact dryer is employed, but other dryers can also be used.

Further, by providing two or more outlets for a dryer that is designed to be attached to a wall, etc., a plurality of shoes can be sterilized and deodorized at one time.

A large dryer according to the present invention can be installed in a sterilizing and deodorizing room of a gymnasium, so that it can process, at one time, multiple items of sportswear, such as sports shoes and training wear, after they have been used.

Further, a timer can be provided for a dryer according to the present invention, so that a time can be selected in advance for the automatic sterilization and deodorization of objects.

As shown in FIG. 1, a dryer according to the present invention can be so designed that the ceramic body 5, which is impregnated with an alkaline chlorine dioxide solution, is coupled with the ceramic body 6, which is impregnated with an acid solution, such as a citric acid solution.

In this case, the ceramic body 5 that is impregnated with the alkaline chlorine dioxide solution is located adjacent to the outlet 2 of the dryer, and the ceramic body 6 that is impregnated with the citric acid solution is located adjacent to the heater 3.

When a heated air stream is passed through holes 7 (see FIGS. 3 to 10) in the ceramic bodies 5 and 6, chlorine dioxide gas is more effectively liberated, and the effects of the deodorization, sterilization, and mold prevention on objects, such as shoes, are further increased and an excellent immediate effect is provided.

The ratio of the volume of the ceramic body 5, which is impregnated with the stabilized chlorine dioxide solution, to the volume of the ceramic body 6, which is impregnated with the citric acid solution, is preferably about 7:3. Although, in this case, citric acid is used in the solution with which the ceramic body is impregnated, there are other acids that can be used in its place.

Figure 4:
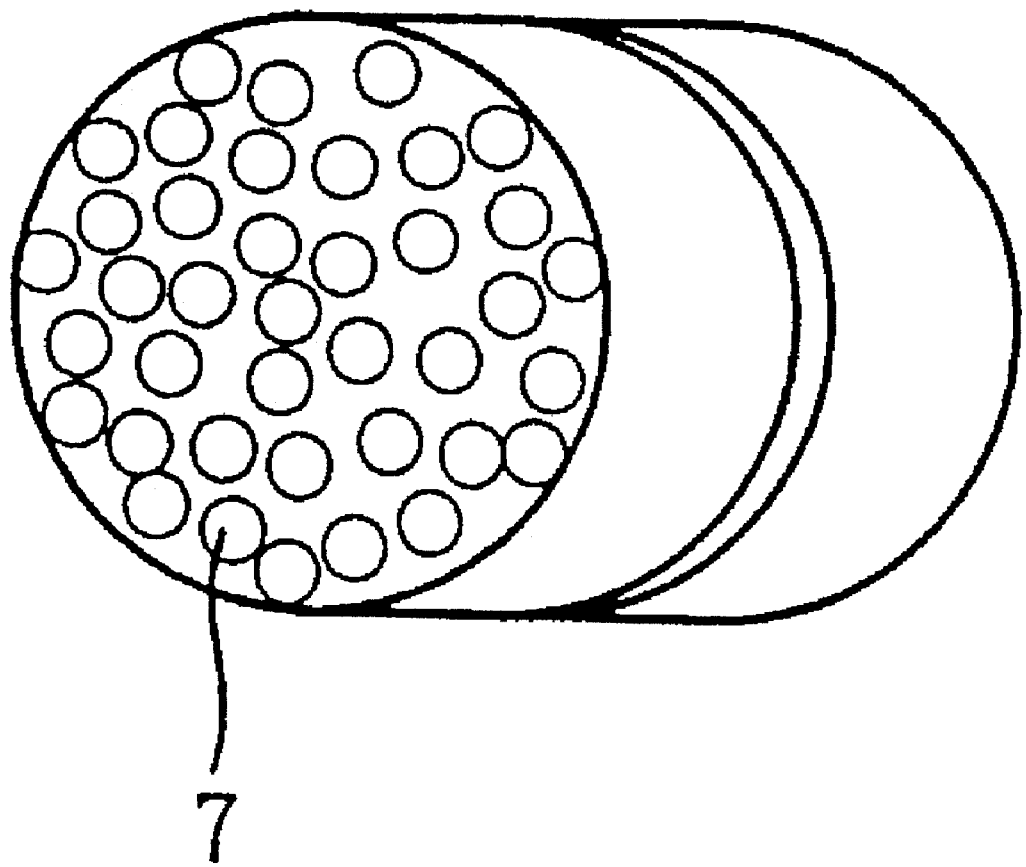
FIG. 4 is a perspective view of an example where a solution supply groove is formed in the first example of a detachable ceramic body that is used in the dryer of the present invention.
Figure 5:
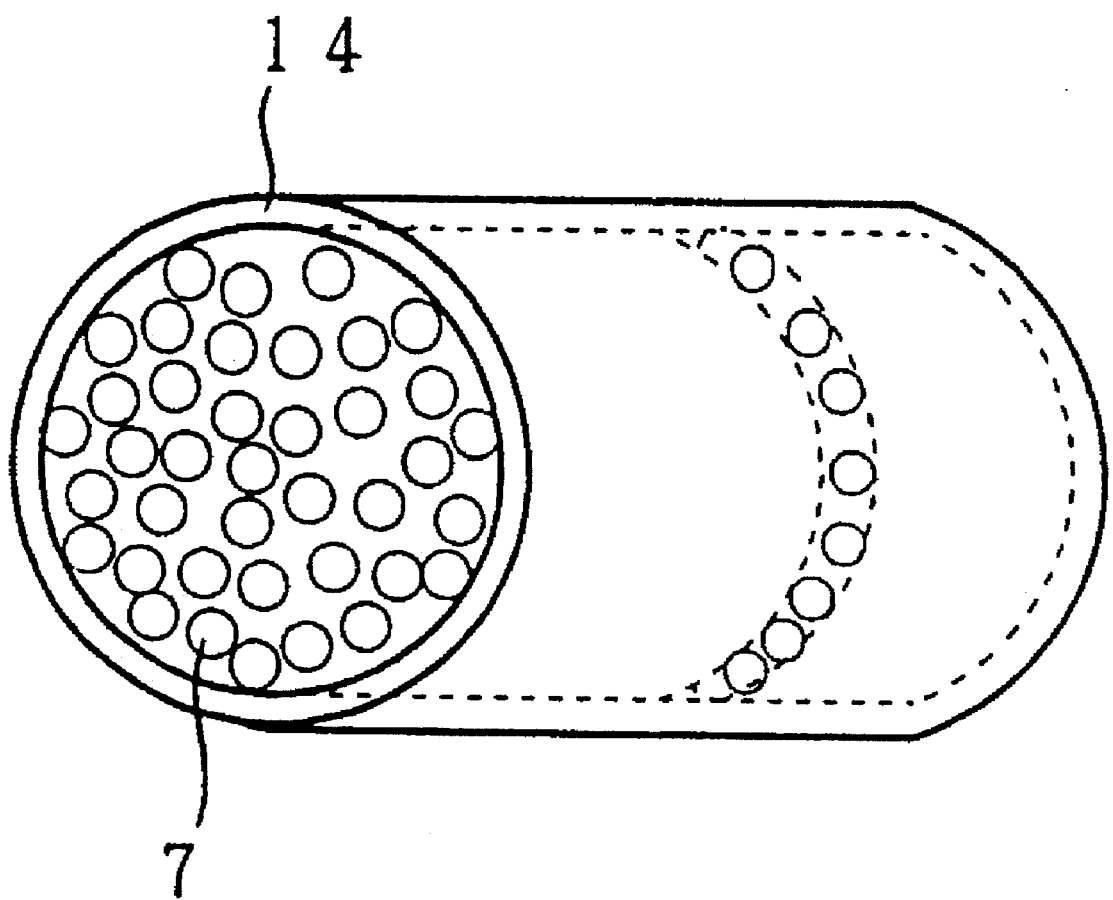
FIG. 5 is a perspective view of an example in which are combined two of the first example of a detachable ceramic body, which is used in the dryer of the present invention.
Figure 6:
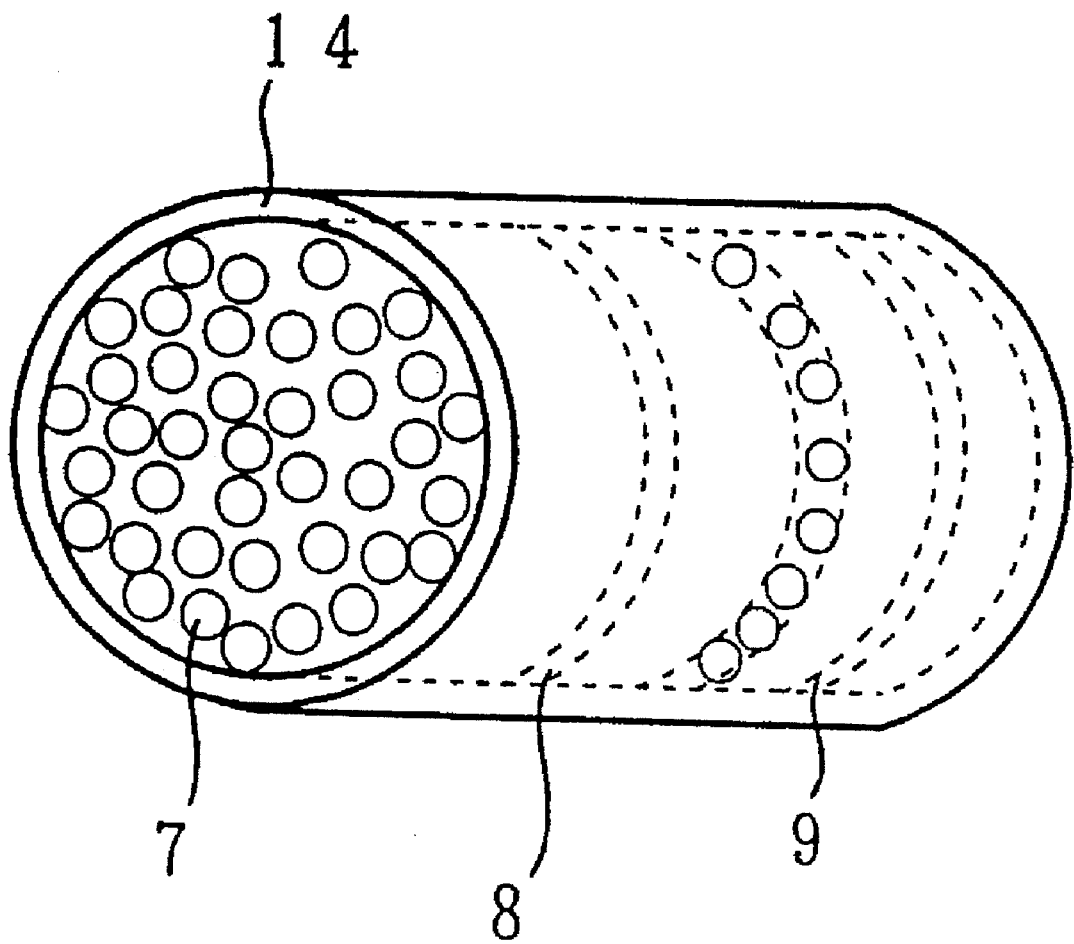
FIG. 6 is a perspective view of an example in which are combined two of the first example of a detachable ceramic body having a solution supply groove, which is used in the dryer of the present invention.
Figure 8:
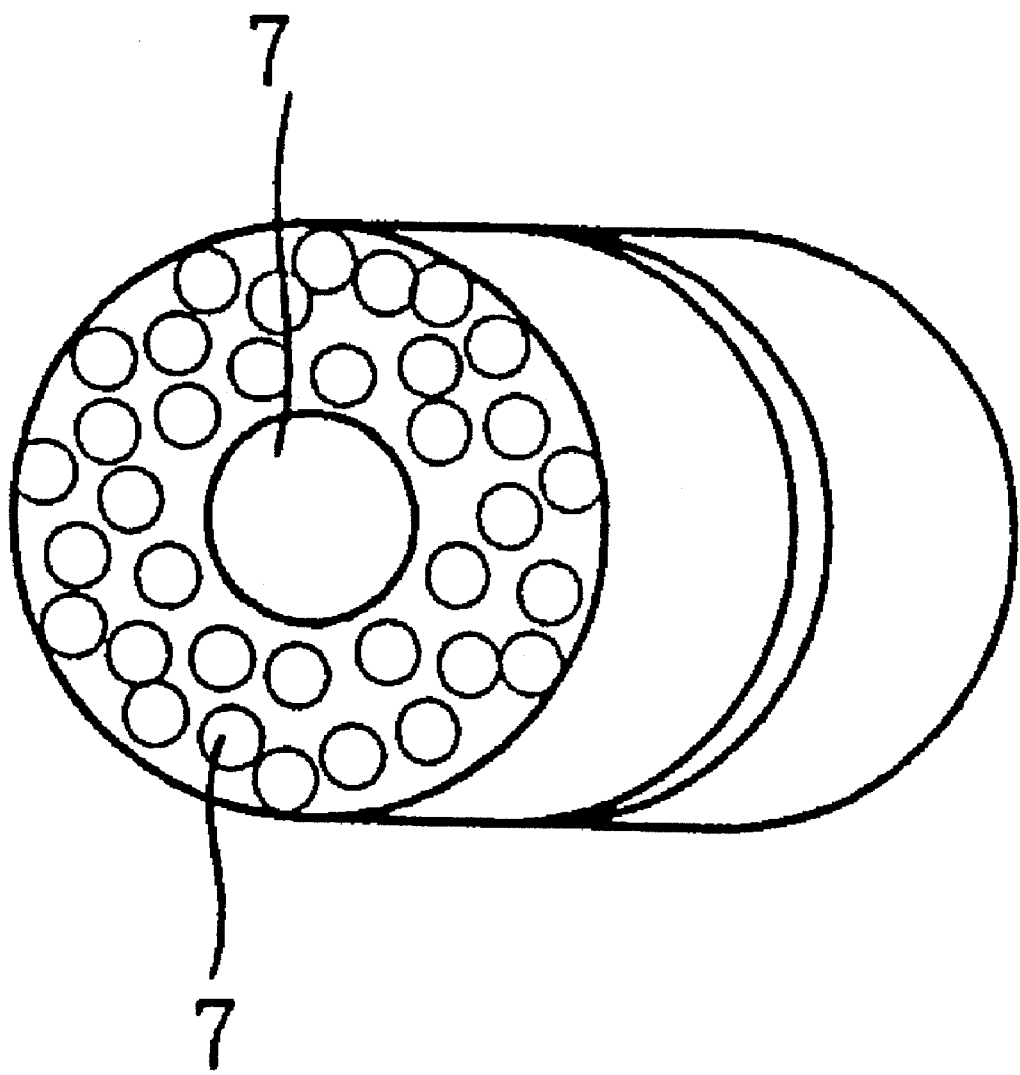
FIG. 8 is a perspective view of an example where a solution supply groove is formed in the second example of a detachable ceramic body that is used in the dryer of the present invention.
Figure 9:
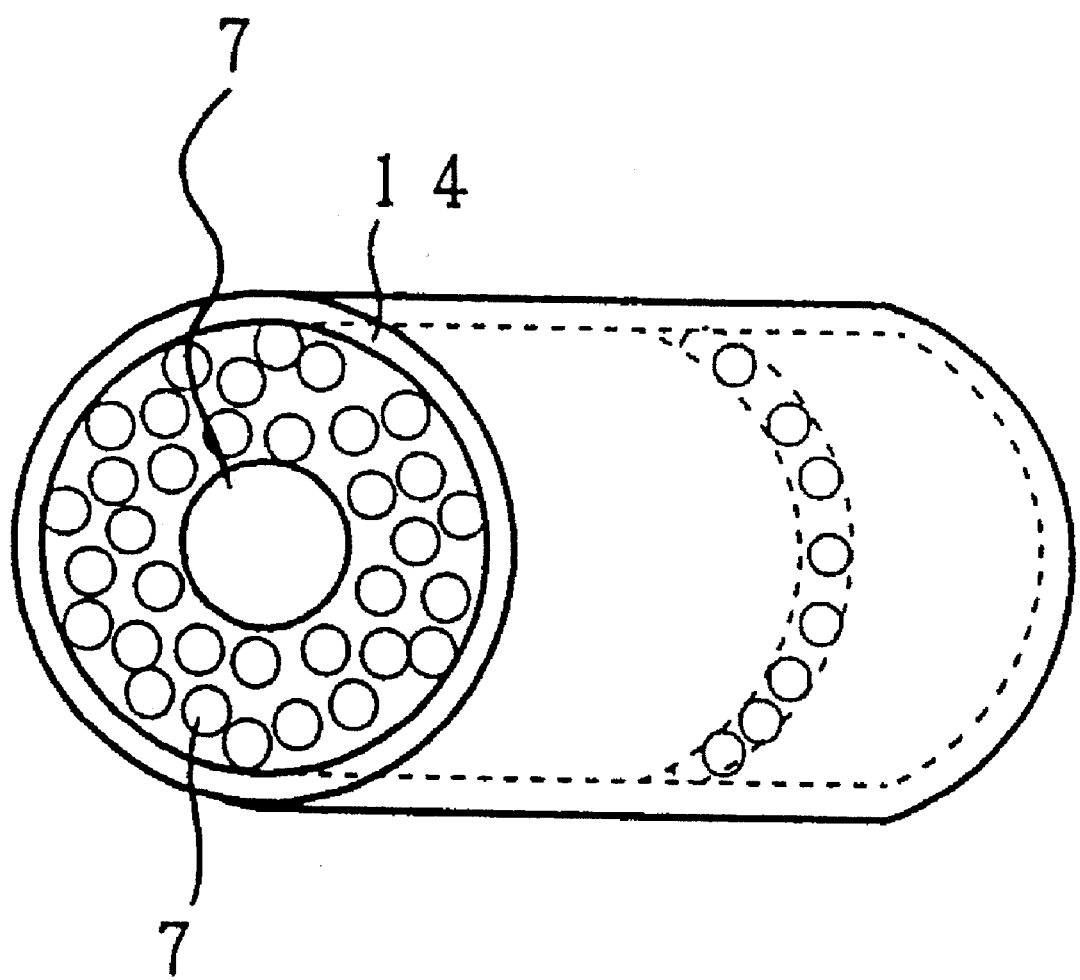
FIG. 9 is a perspective view of an example in which are combined two of the second example of a detachable ceramic body, which is used in the dryer of the present invention.
Figure 10:
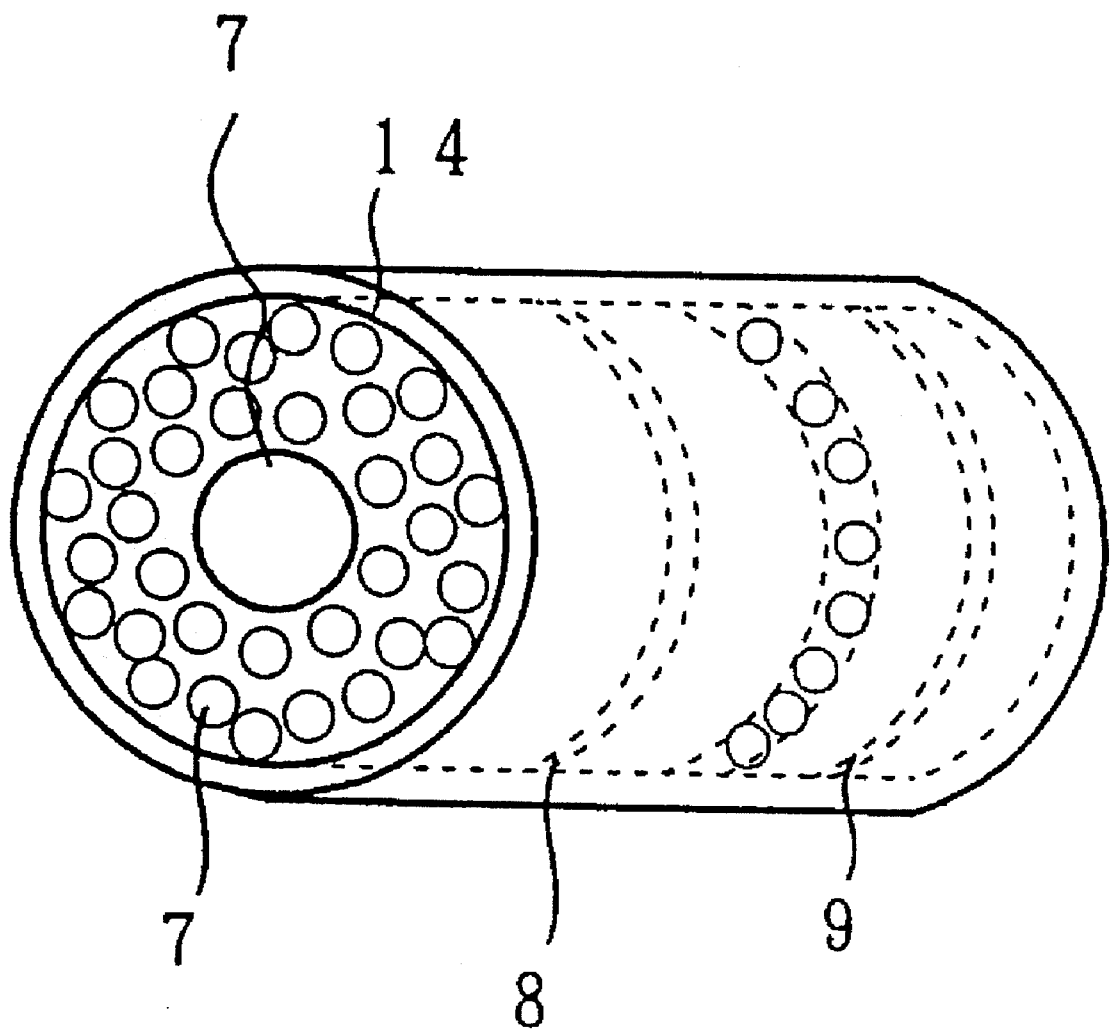
FIG. 10 is a perspective view of an example in which are combined two of the second example of a detachable ceramic body having a solution supply groove, which is used in the dryer of the present invention.

In addition, as is shown, for example, in FIGS. 2, 4, and 8, according to the present invention, a chlorine dioxide solution supply device 10 that supplies an alkaline chlorine dioxide solution to the ceramic body 5 is provided, and a chlorine dioxide solution supply groove 8 along which the alkaline chlorine dioxide solution is supplied by the chlorine dioxide solution supply device 10 is formed around the circumference of the side surface of the ceramic body 5.

Provided for the other ceramic body 6 is, for example, a citric acid solution supply device 11 that supplies a citric acid solution, and a citric acid solution supply groove 9, along which the citric acid solution is supplied by the citric acid solution supply device 11, is formed around the circumference of the side surface of the ceramic body 6.

In this invention, the chlorine dioxide solution supply device 10 and the citric acid solution supply device 11 are arranged in parallel or in series on the upper portion of the dryer 1, for example, as shown in FIG. 2.

The supply devices 10 and 11 supply an alkaline chlorine dioxide solution and a citric acid solution along the supply grooves 8 and 9, respectively, in the ceramic bodies. The ceramic bodies 5 and 6 are impregnated with the chlorine dioxide solution and the citric acid solution that is supplied along the respective supply grooves 8 and 9, and warm air is blown through the through holes 7 (see FIGS. 3 to 10), which are provided in the ceramic bodies, so that an air stream containing a chlorine dioxide gas is generated.

With such an arrangement, the replacement period for the ceramic bodies can be extended, and the effects of sterilization, deodorization, mold prevention or the like can be increased.

The ceramic bodies 5 and 6 are usually columnar, for example, cylindrical, and a plurality of the through holes 7 are provided in their cross sections in the longitudinal direction. It is desirable that multiple through holes 7 be provided for good ventilation.

Figure 3:
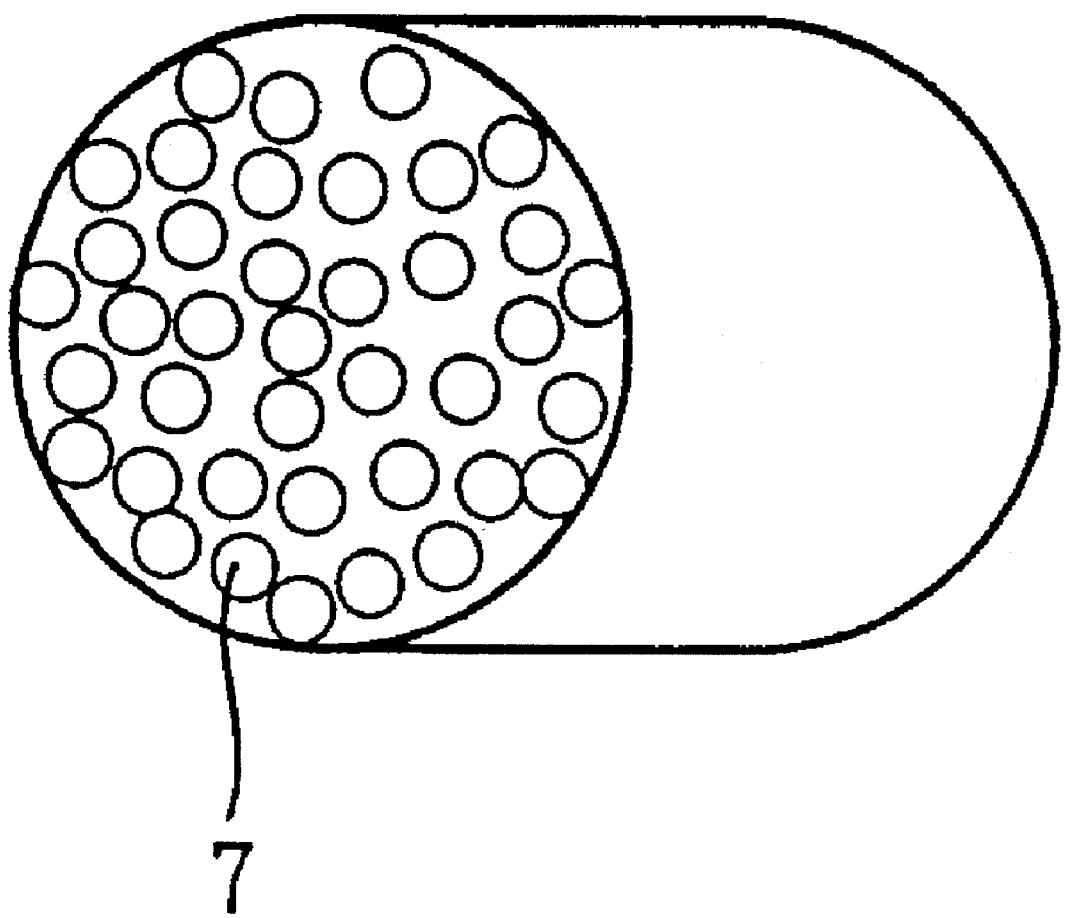
FIG. 3 is a perspective view of a first example of a detachable ceramic body that is used in the dryer of the present invention.

When many of the comparatively small through holes 7 that have an identical diameter are provided longitudinally in the ceramic bodies 5 and 6, as is shown in the cross section in FIG. 3, an air stream that passes through the through holes 7 contains more chlorine dioxide gas, and the deodorizing and sterilizing effects are accordingly increased.

In addition, a through hole 7 having a large diameter is provided in the center of the cross section of each of the ceramic bodies 5 and 6, and many through holes having a smaller diameter are arranged around the large through hole.

With this arrangement, the backflow to the heater 3 of an air stream that contains a chlorine dioxide gas can be prevented.

When the ceramic body 6 that is impregnated with the citric acid solution and the ceramic body 5 that is impregnated with the chlorine dioxide solution are coupled together by using paper or non woven fabric, as shown in FIGS. 5, 6, 9, and 10, to reinforce their connection, the effect provided by the present invention can be increased.

It is preferable that the ceramic bodies 5 and 6 be detachable from the dryer body 1; for example, a cartridge type unit should be provided. In this case, after it has been used for a specified period (e.g., one to three months), the ceramic body can be replaced with a new ceramic adsorbent that is impregnated with chlorine dioxide.

It is preferable that the alkaline chlorine dioxide solution supply device 10 and the citric acid solution supply device 11 also be detachable from the dryer body. With this structure, the solution supplement can be facilitated, and the supply devices 10 and 11 can easily supply the alkaline chlorine dioxide solution and the citric acid solution, respectively.

Figure 11:
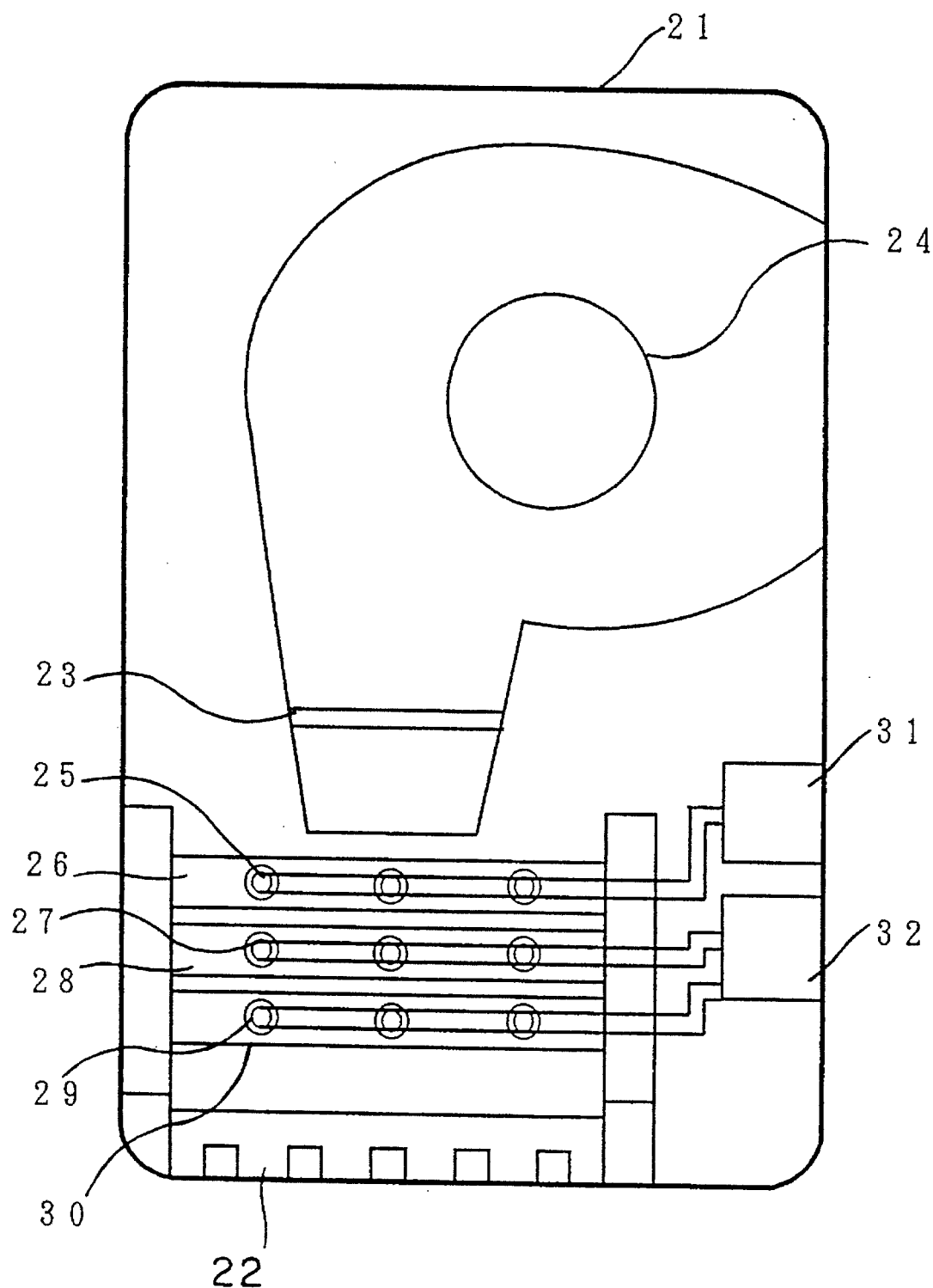
FIG. 11 is a cross sectional view of a schematic structure of an example of a dryer (air towel) according to the present invention.

In FIG. 11, reference number 21 denotes an air towel body; 22, an outlet; 23, a heater; 24, a fan; 25, a ceramic body that is impregnated with a citric acid solution; and 26, a first member to which are attached three ceramic bodies that are impregnated with a citric acid solution.

Reference numbers 27 and 29 denote ceramic bodies that are impregnated with an alkaline chlorine dioxide solution; and 28 and 30, second and third members to each of which are attached three ceramic bodies that are impregnated with an alkaline chlorine dioxide solution.

Reference number 31 denotes a citric acid solution supply device; 32, an alkaline chlorine dioxide solution supply device; 33 (see FIGS. 12 through 15), a hollow pipe; 34 (see FIGS. 12 through 15), small holes that are formed in the hollow pipe 33; 35, a through hole that is formed along the interior of each of the ceramic bodies so as to communicate with the hollow pipes 33, which are inserted into opposite ends of the ceramic body; and 36, an external frame member to which the columnar ceramic bodies are attached.

In the dryer (air towel) shown in FIG. 11, the first member 26, to which is attached three ceramic bodies 25 that are impregnated with the citric acid solution, is provided between the heater 23 and the outlet 22 that is adjacent to the heater 23.

Below the first member 26 are provided the second and third members 28 and 30 to which are respectively attached three ceramic bodies 27 and 29 that are impregnated with the alkaline chlorine dioxide solution.

Warm air that is heated by the heater 23 flows toward the outlet 22 while contacting the ceramic bodies 25, which are impregnated with the citric acid solution, and the ceramic bodies 27 and 29, which are impregnated with the alkaline chlorine dioxide solution.

Figure 12:
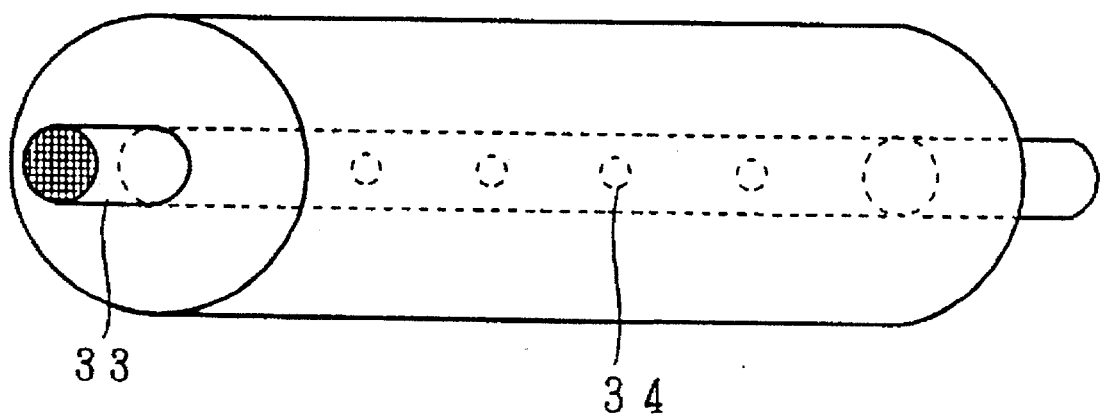
FIG. 12 is a perspective diagram illustrating a first example arrangement of a ceramic body according to the present invention.

As shown in FIG. 12, the ceramic body is, for example, cylindrical, and the hollow pipe 33, which is made of, for example, stainless steel and in which many small holes 34 are formed, is inserted into the center of the ceramic body.

Figure 13:
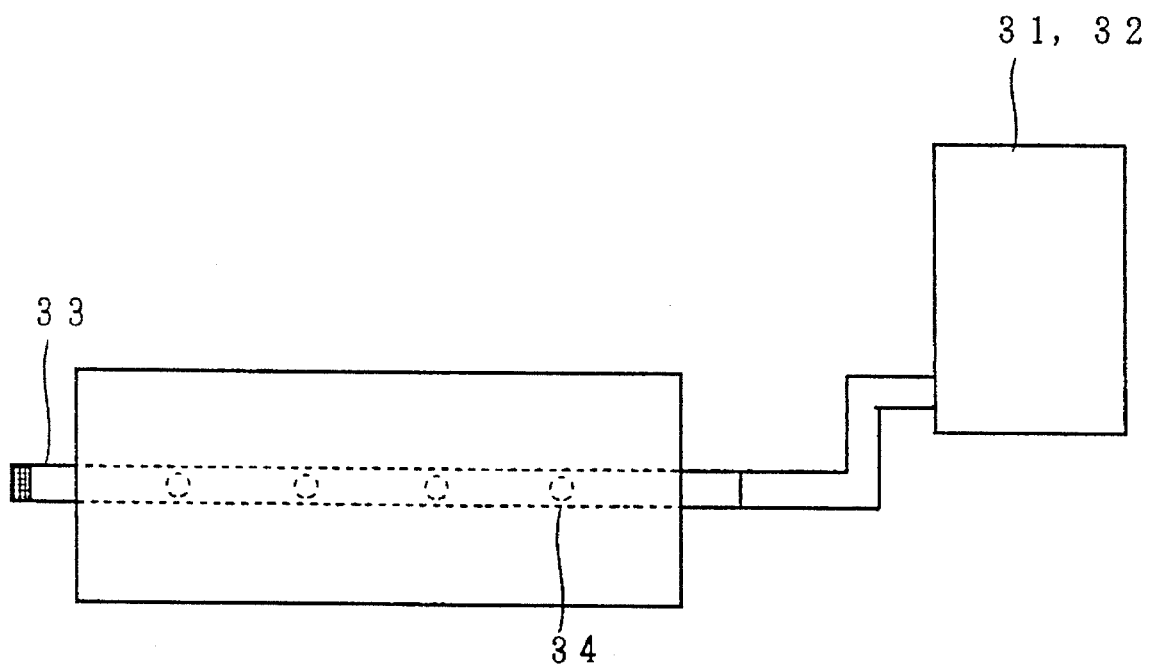
FIG. 13 is a diagram showing an example structure where a solution is supplied by a solution supply device to the ceramic body of the first example arrangement according to the present invention.

As shown in FIG. 13, the citric acid solution, or the alkaline chlorine dioxide solution, from the supply device 31, or 32, in FIG. 11, is supplied to one end of the hollow pipe 33, passes through the small holes 34, which are formed in the pipe 33, and is absorbed by the ceramic body.

Figure 14:
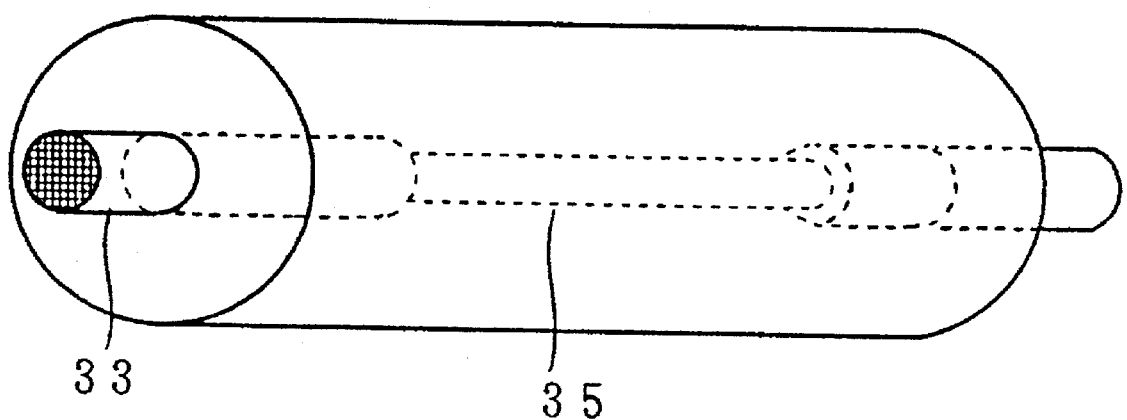
FIG. 14 is a perspective diagram illustrating a second example arrangement for the ceramic body according to the present invention.

The ceramic body according to the present invention, which is cylindrical, for example, as is shown in FIG. 14, has one of the hollow pipes 33 inserted into each end and has the through hole 35 formed in its center to communicate with both of the pipes 33.

Figure 15:
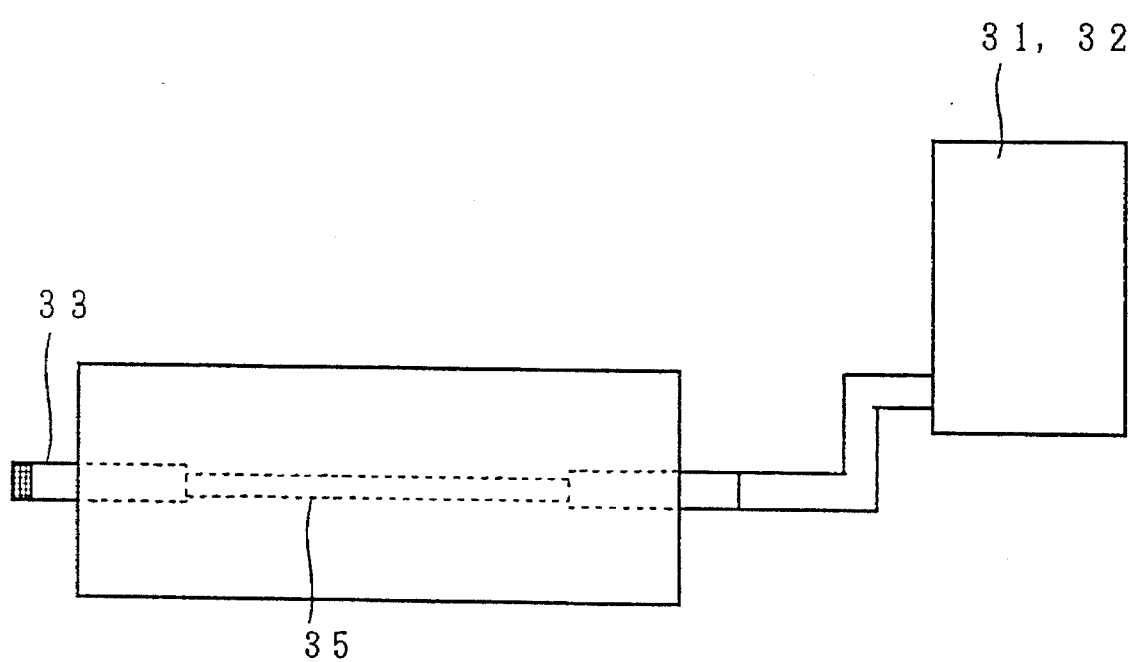
FIG. 15 is a diagram showing an example structure where a solution is supplied by a solution supply device to the ceramic body of the second example arrangement according to the present invention.

As shown in FIG. 15, the citric acid solution, or the alkaline chlorine dioxide solution, from the supply device 31, or 32, in FIG. 11, is supplied to one of the hollow pipes 33, passes through the through hole 35, which is formed in the ceramic body, and is absorbed by the ceramic body.

In FIG. 15, the pipe 33 is hollow because the citric acid solution and the alkaline chlorine dioxide solution are to be supplied from the citric acid solution supply device 31 and the alkaline chlorine dioxide solution supply device 32, respectively.

The end of one of the pipes 33 is coupled with the citric acid solution supply device 31 or the alkaline chlorine dioxide solution supply device 32, while the end of the other pipe 33 is sealed to prevent leakage of the citric acid solution or the alkaline chlorine dioxide solution.

An absorbent ceramic body that has numerous pores absorbs a solution well due to capillarity and thus accelerates the permeation of the solution. The absorbent ceramic body also accelerates the generation of a chlorine dioxide gas when warm air contacts it.

Figure 16:
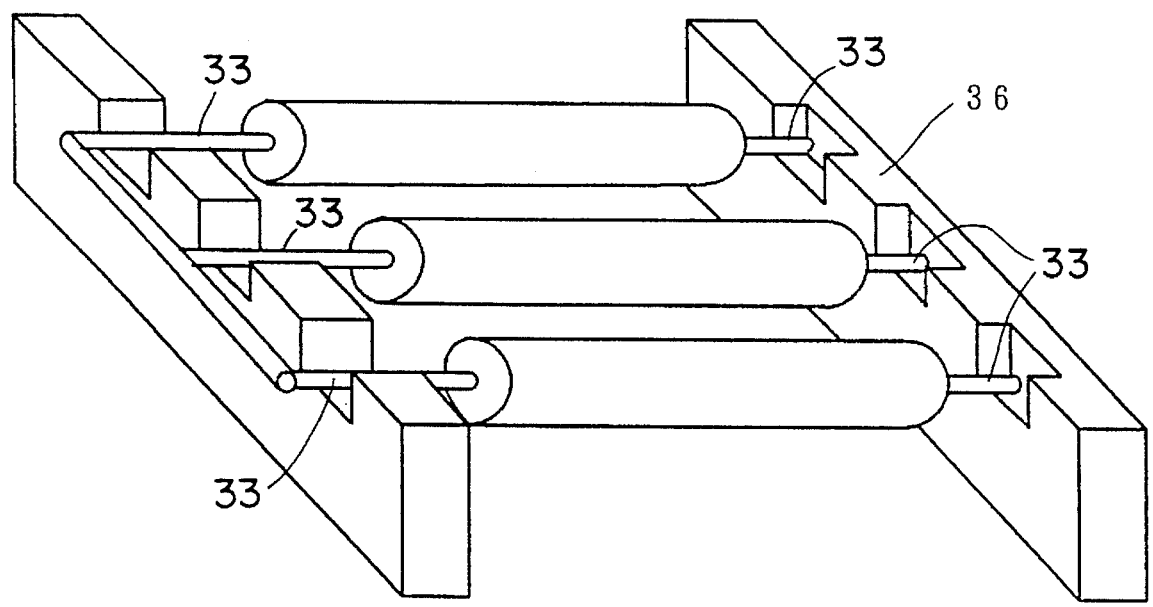
FIG. 16 is a perspective view illustrating a schematic arrangement of the members to which the ceramic bodies are attached.

To arrange the ceramic body in the air towel body 21, as is shown in FIG. 16, the hollow pipes 33 that project from both ends of the ceramic body are detachable from the external frame member 36.

In FIG. 11, the first member 26, where the ceramic bodies impregnated with the citric acid solution are attached to the external frame 36 in FIG. 16, is provided adjacent to the heater 23, and the second and third members 28 and 30, where the ceramic bodies impregnated with the alkaline chlorine dioxide solution are attached respectively to the external frames 36, are provided adjacent to the outlet 22, so that these members are positioned perpendicular to an air stream.

Since the first member 26, which is impregnated with the citric acid solution, is positioned higher and nearer the source of the air stream than are the second and third members 28 and 30, which are impregnated with the alkaline chlorine dioxide solution, the liberation of chlorine dioxide gas is accelerated and the chlorine dioxide gas content of the warm air can be increased.

It is preferable that the ceramic bodies 25, 27, and 29 be detachable from the air towel body 21; for example, a cartridge type unit should be provided. In this case, after it has been used for a specific period, the ceramic body is replaced with a new ceramic adsorbent.

The air towel of the present invention comprises the citric acid solution supply device 31 that supplies a citric acid solution to the ceramic bodies and the alkaline chlorine dioxide solution supply device 32 that supplies an alkaline chlorine dioxide solution to the ceramic bodies.

The citric acid solution supply device 31 and the alkaline chlorine dioxide solution supply device 32 are provided detachable from the air towel body 21. Thus, supplementation of the solution can be facilitated.

Figure 17:
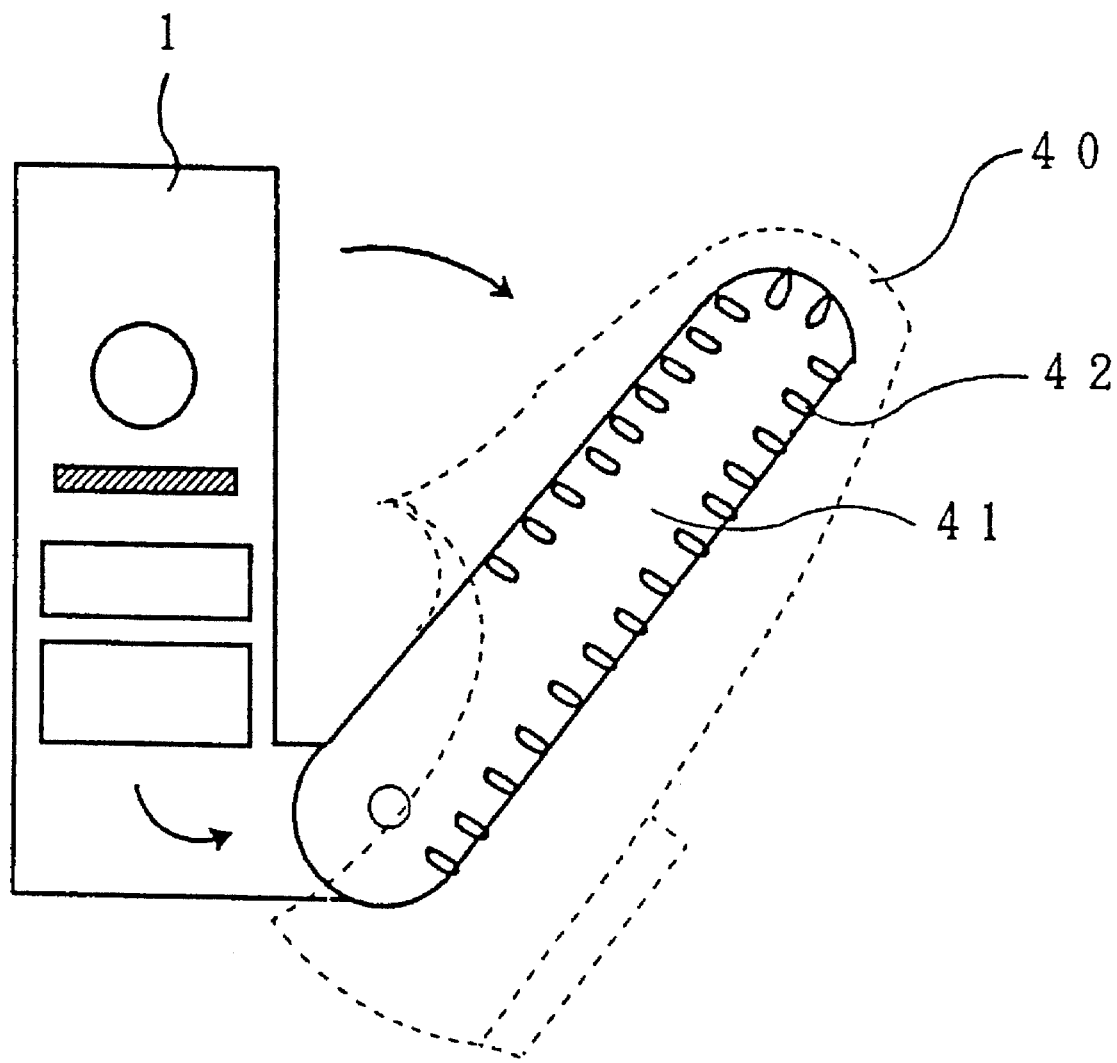
FIG. 17 is a schematic side cross sectional view of an example where a shoe insertion member is attached to the dryer of the present invention.
Figure 18:
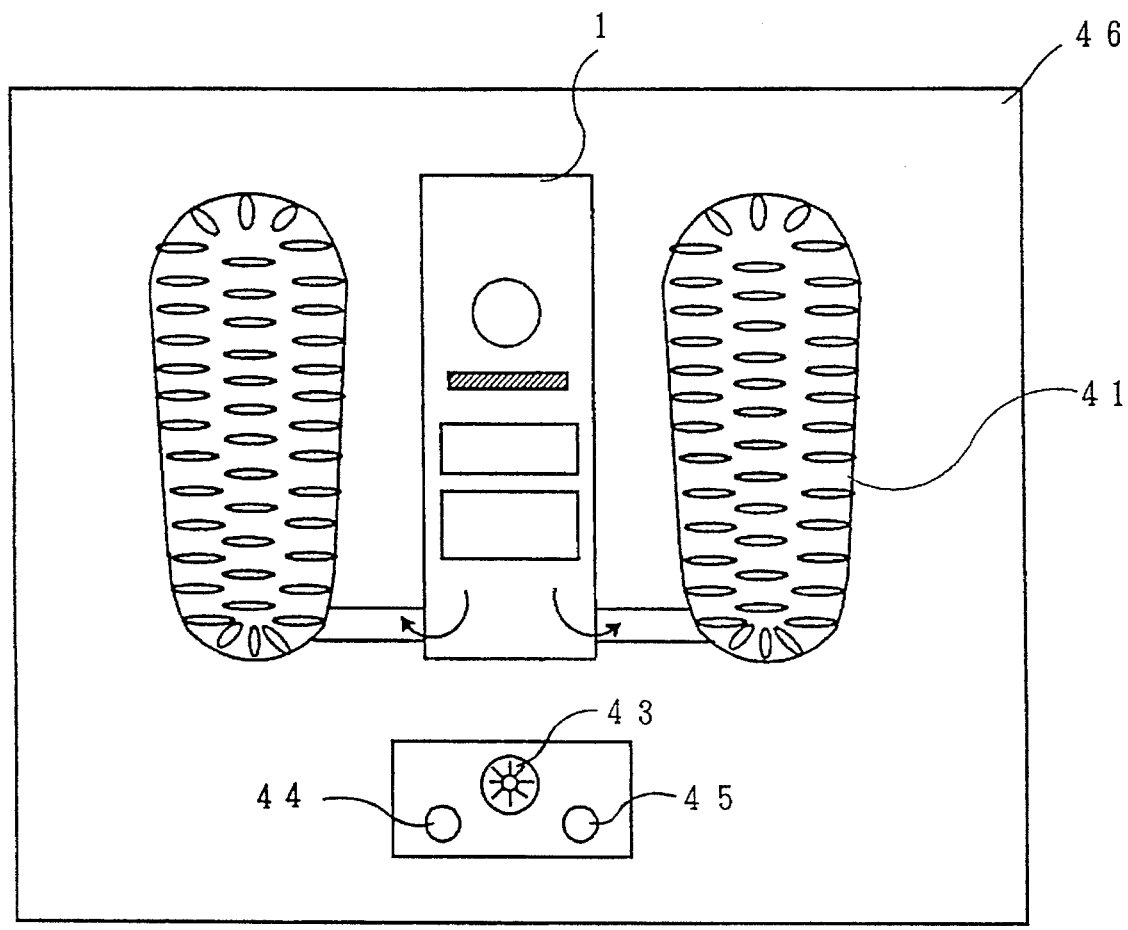
FIG. 18 is a schematic front view of an example where shoe insertion members are attached to the dryer of the present invention.

In FIGS. 17 and 18, reference number 1 denotes a dryer body; 40, a shoe; 41, a shoe insertion member; 42, a plurality of small holes formed in the shoe insertion member 41; 43, a timer; 44, a dryer power switch; 45, a shoe insertion member manipulation switch; and 46, a wall.

As shown in FIG. 17, the dryer 1 of the present invention may be fitted with the movable hollow shoe insertion member 41, in which are the small holes 42, that communicates with the outlet of the dryer 1. The dryer body 1 may be attached to a wall, etc., and more than one shoe insertion member 41 may be installed.

Warm air that is supplied by the dryer 1 travels from the outlet through the shoe insertion member 41 and is discharged from the small holes 42 formed therein, so that the inside of a shoe 40 is deodorized and sterilized.

To perform deodorization and sterilization, the shoe insertion member 41, as is indicated by the arrow in FIG. 17, is pulled to the front from the dryer body 1, which is attached to the wall 46, etc., and the shoe 40 is slipped over the shoe insertion member 41. The dryer is then powered by the dryer power switch 44.

The shoe insertion member 41 can be pulled out manually or extended electrically by the shoe insertion member manipulation switch 45. The deodorization and sterilization processing time can be controlled by the timer 43.

With the above described arrangement, simultaneous deodorization, sterilization, and mold prevention can be automatically performed for a plurality of shoes, a feature that is very suitable for athletic clubs, gymnasiums, etc.

The above described example has employed the first member where three ceramic bodies impregnated with the citric acid solution are provided, and the second and third members where three ceramic bodies impregnated with the alkaline chlorine dioxide solution are provided. However, the number of the ceramic bodies, which are impregnated with a citric acid solution or a chlorine dioxide solution, that are to be attached to the members is optional, and is not limited to three.

Further, in the above described example there is provided one first member, to which are attached the ceramic bodies impregnated with the citric acid solution, and one each of the second and third members, to which are attached the ceramic bodies impregnated with the alkaline chlorine dioxide solution. However, the number of members to which the ceramic bodies are attached is not limited to one each; it is optional.

The dryer of the present invention can easily and efficiently supply a deodorizing and sterilizing air stream.

This air stream effectively deodorizes, sterilizes, and provides mold prevention for various goods and locations: shoes; sports goods, such as protective wear for kendo, boxing gloves, and ski shoes; toys, such as stuffed toys; shoe boxes; dressing lockers; indoor sanitary toilets; refrigerators, etc.

In addition, the warm air stream, which also serves as an air towel, dries wet hands, while at the same time it can sterilize them and can also deodorize them as needed.

EXAMPLE 1

Figure 7:
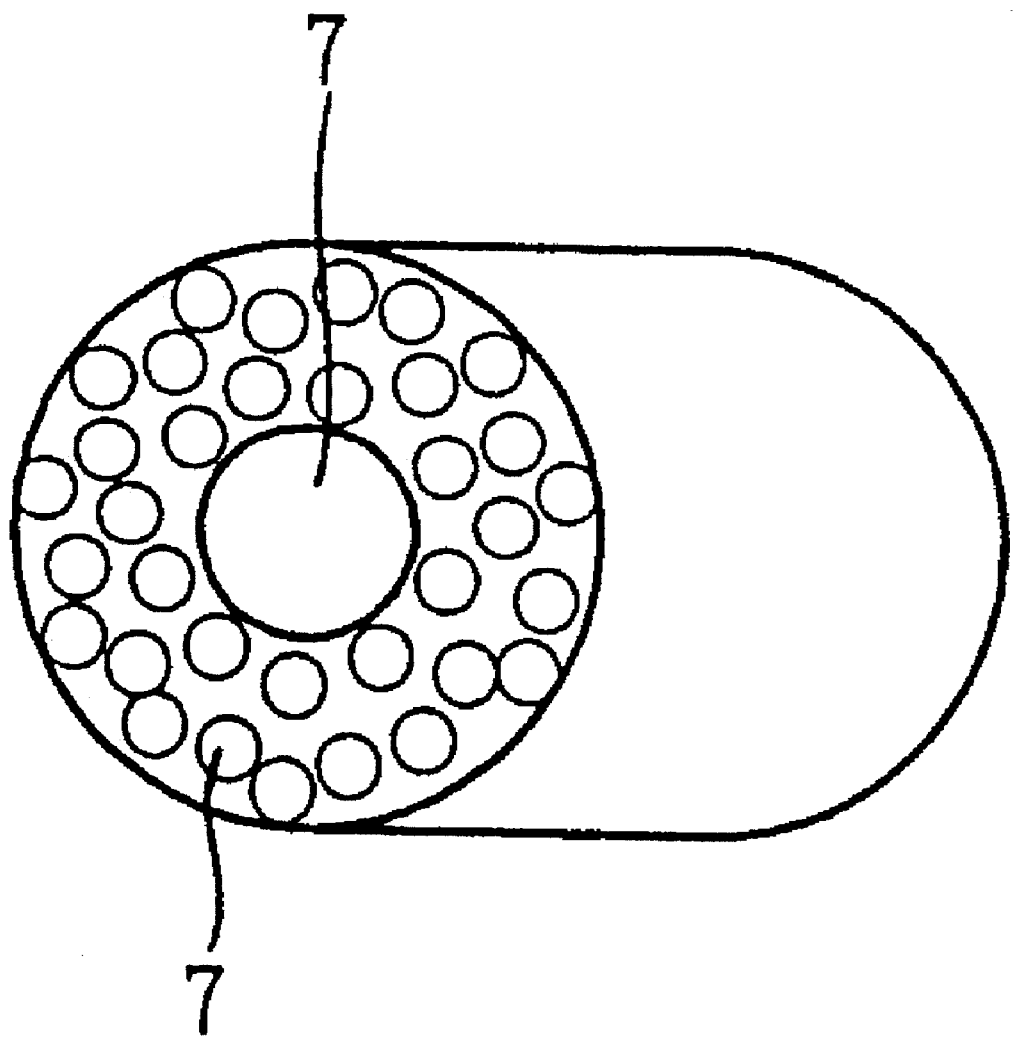
FIG. 7 is a perspective view of a second example of a detachable ceramic body that is used in the dryer of the present invention.

Two different sized mixtures, each of which consisted of 60 weight % of 100-mesh powdered cow bone, 20 weight % of silica, and 20 weight % of alumina, were formed into ceramic bodies as shown in FIG. 7. One ceramic body was approximately 3/1 times as large as the other.

The larger ceramic body 5 thus obtained was heated at 60° C. The resultant ceramic body 5 was immersed in an alkaline chlorine dioxide solution at ordinary temperature for 5 to 10 seconds, and was extracted.

The smaller ceramic body 6 was heated at 60° C. The resultant ceramic body 6 was immersed in a citric acid solution, whose pH was adjusted by a sodium solution to pH 3 or 4, at ordinary temperature for 5 to 10 seconds, and was extracted.

Then, the large ceramic body 5 and the small ceramic body 6 were covered with non-woven fabric and securely coupled.

The large ceramic body 5, i.e., the ceramic body 5 that was impregnated with the alkaline chlorine dioxide solution, was installed adjacent to the outlet 2 of the dryer. The small ceramic body 6, i.e., the ceramic body 6 that was impregnated with the citric acid solution, was installed adjacent to the heater 3 of the dryer.

An air stream that was heated to a temperature of 50° C. while passing through the fan 4 and the heater 3 flowed in the through holes 7 in the ceramic bodies 5 and 6, so that an air stream containing chlorine dioxide was generated.

When this air stream was discharged for 4 to 6 minutes each morning and evening into shoes that had been worn, the shoes were dried and there were no bad odors. Over a period of four days, shoes that were worn by a person with athlete's foot were processed morning and evening, as is described above, and continued to be odor-free and dry.

EXAMPLE 2

Bacteria (*Escherichia coli* ATCC 8739 and *Staphylococcus aureus* (MRSA) HIC 2011) were cultivated in 5 ml of a soy bean-casein-digest (SCD) liquid medium at 37° C. for 24 hours. Yeasts (*Candida albicans* ATCC 10231) were cultivated in 5 ml of a glucose peptone (GP) liquid medium at 37° C. for 24 hours. Molds (Cladosporium) were cultivated in a potato-dextrose (PD) agar-agar medium at 27° C. for one week. For the test, a bacterial solution that was diluted $10^2$ to $10^3$ times and a dilute solution of about $10^6$/ml of yeasts and molds were employed.

The stabilized chlorine dioxide solution was diluted to 1500 ppm. A natural calcium ceramic body that was impregnated with that diluted solution was positioned on the outlet side of the dryer. A natural calcium ceramic body that was impregnated with a 5% citric acid solution (where the pH was adjusted to 3 or 4 by an alkali) was positioned on the heater side of the dryer.

Paper discs (diameter 9 mm) were permeated with 0.06 ml of the prepared bacteria liquids, and warm air at about 40° C. driven from the dryer was discharged onto each of the paper discs for approximately 3.5 minutes.

Then, bacteria from the individual paper discs that were impregnated with the prepared germ solutions were employed to inoculate 10 ml of the SCD liquid medium, and Eumycetes were employed to inoculate 10 ml of the GP liquid medium. The inoculated media were cultivated at 35° C. for 48 hours and then at 27° C. for one week, and were thereafter examined to evaluate the sterilization effect of the dryer of the present invention. As a result, no active bacteria, yeasts, and molds were found.

EXAMPLE 3

Bacteria (*Trichophyton rubrum* IFO 6203) were cultivated in the potato dextrose agar-agar medium at 25° C. for 7 to 14 days. Then, the resultant body was suspended in sterilized water to which 0.05% of polysolvate 80 was added so as to prepare a bacterial liquid in which the bacteria count was $10^4$ to $10^5$/ml. The gauze was permeated using 0.2 ml of the bacterial liquid.

The stabilized chlorine dioxide solution was diluted to 1500 ppm. A natural calcium ceramic body that was impregnated with that diluted solution was positioned on the outlet side of the dryer. A natural calcium ceramic body that was impregnated with a 5% citric acid solution (where the pH was adjusted to 3 or 4 by an alkali) was positioned on the heater side of the dryer.

Air that had been warmed to about 40° C. was discharged by the dryer onto the gauze that had been impregnated with the bacteria solution for five minutes. As a result, after 60 minutes had elapsed following the process, the count of active bacteria was 40; and about four hours later the count was 10 or fewer.

EXAMPLE 4

A mixture that consisted of 60 weight % of cow bone powder of 100 mesh, 20 weight % of silica, and 20 weight % of alumina was prepared, and from the mixture a columnar ceramic body having a diameter of 25 mm was formed. A hollow pipe having a diameter of 10 mm and that was pierced by eight small holes, as is shown in FIG. 12, was inserted into the columnar ceramic body.

Three sets of members, each of which had three such ceramic bodies, were formed and installed in the air towel body shown in FIG. 11. The ceramic bodies provided for the first member were impregnated with a citric acid solution, where the pH was adjusted to 3 or 4 by an alkali, that was supplied by the citric acid solution supply device. The ceramic bodies provided for the second and third members were impregnated with about 1500 ppm of an alkaline chlorine dioxide solution that was supplied by the alkaline chlorine dioxide solution supply device.

Air, which had been heated by the heater 23 at about 40° C. and was driven by the fan 24, contacted and passed through the ceramic bodies, which were respectively impregnated with the citric acid solution and alkaline chlorine dioxide solution. Thereafter, warm air that contained chlorine dioxide gas was discharged from the air outlet. Using the discharged warm air, wet hands could be dried and sterilized.

Various modes of carrying out the invention are contemplated as being within the scope of the following claims that in particular point out and distinctly describe the subject matter that is regarded as the invention.

What is claimed is:

1. A deodorizing and sterilizing dryer comprising:

a housing having an outlet;

a heater and a fan arranged within said housing so that air heated by said heater is forced, by said fan, along an air stream path which lies between said heater and said outlet;

a first ceramic body impregnated with an acid solution; and a second ceramic body impregnated with an alkaline chlorine dioxide solution, said first and second ceramic bodies being positioned along said air stream path downstream of said heater and fan for receiving the heated air forced along the air stream path and for supplying warm air that contains chlorine dioxide gas to said outlet, said ceramic bodies being positioned such that said first ceramic body is adjacent said heater and said second ceramic body is adjacent said outlet.

2. A deodorizing and sterilizing dryer according to claim 1, wherein said first and second ceramic bodies are detachably mounted in said housing.

3. A deodorizing and sterilizing dryer according to claim 1, further comprising an acid solution supply device coupled to said first ceramic body for supplying the acid solution thereto.

4. A deodorizing and sterilizing dryer according to claim 3, wherein said acid solution supply device is detachably mounted on said housing.

5. A deodorizing and sterilizing dryer according to claim 1, further comprising an alkaline chlorine dioxide solution supply device coupled to said second ceramic body for supplying the alkaline chlorine dioxide solution thereto.

6. A deodorizing and sterilizing dryer according to claim 5, wherein said alkaline chlorine dioxide solution supply device is detachably mounted on said housing.

7. A deodorizing and sterilizing dryer according to claim 1, wherein at least one of said ceramic bodies is made of an alkaline ceramic material.

8. A deodorizing and sterilizing dryer according to claim 7, wherein said alkaline ceramic material contains at least one material selected from a group consisting of animal bone powder, shell powder, limestone powder, and coral powder.

9. A deodorizing and sterilizing dryer according to claim 7, wherein said alkaline ceramic material contains animal bone powder.

10. A deodorizing and sterilizing dryer according to claim 7, wherein said alkaline ceramic material contains at least one ceramic selected from a group consisting of silica gel, alumina, and zeolite.

11. A deodorizing and sterilizing dryer according to claim 1, wherein said acid solution contains citric acid.

12. A deodorizing and sterilizing dryer according to claim 1, wherein said acid solution is a citric acid solution and said citric acid solution is at a pH between 2 and 5.

13. A deodorizing and sterilizing dryer according to claim 1, wherein the chlorine dioxide concentration of said chlorine dioxide solution that is used to impregnate said second ceramic body is 500 ppm to 3000 ppm.

14. A deodorizing and sterilizing dryer according to claim 1, wherein at least one of said first and second ceramic bodies is columnar in shape, said columnar shaped ceramic body having a longitudinal dimension, and wherein said dryer further includes a hollow pipe having a perforated pipe wall inserted into said at least one of said ceramic bodies parallel to said longitudinal dimension.

15. A deodorizing and sterilizing dryer according to claim 14, wherein a first frame member, on which is installed a plurality of said columnar shaped ceramic bodies impregnated with said acid solution to form first ceramic bodies, is positioned adjacent to the heater, and a second frame member and a third frame member, on each of which is installed a plurality of said columnar shaped ceramic bodies impregnated with said alkaline chlorine dioxide solution to form second ceramic bodies, are positioned adjacent to the outlet, so that said first, second, and third frame members and said ceramic bodies intersect an air stream of said air stream path.

16. A deodorizing and sterilizing dryer according to claim 1, wherein the shape of at least one of said first and second ceramic bodies is columnar, said at least one of said ceramic bodies having a pair of ends, and wherein hollow pipes are inserted into the ends of said at least one of said ceramic bodies and are connected by a through hole provided in said ceramic body.

17. A deodorizing and sterilizing dryer according to claim 1, further defined as a deodorizing and sterilizing air towel dryer.

18. A deodorizing and sterilizing dryer according to claim 1, wherein at least one of said first and second ceramic bodies has a columnar shape, said columnar shaped ceramic body having a longitudinal dimension and wherein said columnar shaped ceramic body has a plurality of longitudinal through holes.

19. A deodorizing and sterilizing dryer according to claim 18, wherein a plurality of identically shaped, longitudinal through holes are arranged in said at least one of said ceramic bodies.

20. A deodorizing and sterilizing dryer according to claim 18, wherein said plurality of longitudinal through holes includes a central longitudinal through hole that has a given diameter and which is positioned in the center of said columnar shaped ceramic body, and a plurality of longitudinal through holes that have a diameter smaller than said central through hole, which are positioned around said central through hole.

21. A deodorizing and sterilizing dryer according to claim 1, wherein at least one of said first and second ceramic bodies has a columnar shape.

22. A deodorizing and sterilizing dryer according to claim 1, wherein at least one of said ceramic bodies is columnar, and a supply groove for said acid solution or said chlorine dioxide solution, respectively, is formed around the circumference of said columnar ceramic body.

23. A deodorizing and sterilizing dryer according to claim 1, wherein said first ceramic body that is impregnated with said acid solution is securely coupled to said second ceramic body that is impregnated with said alkaline chlorine dioxide solution.

24. A deodorizing and sterilizing dryer according to claim 23, wherein paper and/or non woven fabric is wrapped around said first and second ceramic bodies to securely couple said first ceramic body to said second ceramic body.

25. A deodorizing and sterilizing dryer according to claim 1, further defined as a dryer for deodorizing or sterilizing a product, or preventing mold on a product.

26. A deodorizing and sterilizing dryer according to claim 1, further comprising a plurality of hollow shoe insertion members, each of which has a plurality of small holes, said shoe insertion members communicating with said outlet of said housing.

27. A deodorizing and sterilizing dryer according to claim 1, further defined as installed in a bed pad drying machine.

28. A deodorizing and sterilizing dryer according to claim 1, further defined as installed in an air cleaner.

29. A deodorizing and sterilizing dryer according to claim 1, further defined as is installed in an air conditioner.

* * * * *